United States Patent [19]

Duffett

[11] Patent Number: Plant 5,401

[45] Date of Patent: Feb. 5, 1985

[54] CHRYSANTHEMUM PLANT NAMED VENTURE

[75] Inventor: William E. Duffett, Salinas, Calif.

[73] Assignee: Yoder Brothers, Inc., Barberton, Ohio

[21] Appl. No.: 463,922

[22] Filed: Feb. 4, 1983

[51] Int. Cl.[3] ..... A01H 5/00

[52] U.S. Cl. ..... Plt./78

[58] Field of Search ..... Plt./78–79

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum plant named Venture having flat capitulum form; decorative capitulum type; deep yellow ray floret color; diameter across face of capitulum ranging from 65 to 75 mm. at maturity; uniform nine week photoperiodic flowering response to short days; tall plant height when grown single stem; 12 to 15 cm. peduncles on open, normally terminal sprays; and 13° C. minimum temperature tolerance for initiation and development of flowring buds.

3 Drawing Figures

The present invention comprises a new and distinct cultivar of *Chrysanthemum morifolium,* Ramat., named Venture.

Venture is a product of a planned breeding program which had the objective of creating new chrysanthemum cultivars having low temperature tolerance for cut spray mum programs with decorative capitulum type, yellow ray floret color, nine week flowering response, and the ability to produce commercially acceptable quality in year round programs. Such traits in combination were not present or needed improvement in previously available commercial cultivars.

Venture was originated from a cross made in a controlled breeding program in Salinas, Calif. in 1978. The female parent was identified as 7030220, an unnamed light bronze decorative seedling originated from a hybridization of Solorama, disclosed in U.S. Plant Pat. No. 3,673, and an unnamed seedling. The male parent of Venture was identified as 761881, an unnamed bronze decorative seedling originated from a cross between two unnamed seedlings.

Venture was discovered and selected as one flowering plant within the progeny of the stated cross by William E. Duffett on Sept. 9, 1979 in a controlled environment in Salinas, Calif.

The first act of asexual reproduction of Venture was accomplished when vegetative cuttings were taken from the initial selection in December 1979 in a controlled environment in Salinas, Calif. by a technician working under formulations established and supervised by William E. Duffett.

Horticultural examination of selected units initiated June 1980 has demonstrated that the combination of characteristics as herein disclosed for Venture are firmly fixed and are retained through successive generations of asexual reproduction.

Venture has not been observed under all possible environmental conditions. The phenotype may vary significantly with variations in environment such as temperature, light intensity, and day length. The following observations, measurements and comparisons describe plants grown in Salinas, Calif. and Leamington, Canada under greenhouse conditions which approximate those generally used in commercial practice.

The following traits have been repeatedly observed and are determined to be basic characteristics of Venture which in combination distinguish this chrysanthemum as a new and distinct cultivar:

(1) Flat capitulum form;

(2) Decorative capitulum type;

(3) Deep yellow ray floret color with minimal color oxidation;

(4) Diameter across face of capitulum ranging from 65 to 75 mm. at maturity;

(5) Uniform nine week photoperiodic flowering response to short days;

(6) Medium peduncle length, ranging from 12 to 15 cm.;

(7) Tall plant height, requiring 1–2 long day weeks prior to short days to attain a flowered plant height of 80 to 90 cm. for May through October flowerings; and (8) Low temperature tolerance of 13° C. (55° F.) for initiation and development when grown in single stem cut spray programs with a continuous dark period of 13 to 14 hours.

The accompanying photographic drawings show typical inflorescence and foliage characteristics of Venture, with the colors being as nearly true as possible with illustrations of this type. Sheet 1 is a color photograph of Venture grown as a single stem cut spray. Sheet 2 is a black and white photograph of three views of the inflorescence of Venture. Sheet 3 is a black and white photograph showing the leaves of Venture at three stages of development (mature, intermediate, immature).

Of the many commercial cultivars known to the present inventor, the most similar in comparison to Venture is the unpatented cultivar Golden Polaris. Reference is made to attached Chart A which compares certain characteristics of Venture to those same characteristics of Golden Polaris.

In comparison to Golden Polaris, Venture has deeper yellow ray floret color, with a slower rate of oxidation; its spray formation is generally terminal and similar to Golden Polaris, with shorter peduncles; it has a similar diameter across the face of the capitulum, and an improved tolerance of 13° C. temperature which results in a faster flowering response of approximately one week during fall, winter and spring.

In the following description, color references are made to The Royal Horticultural Society Colour Chart. The color values were determined between 2:15 P.M.

and 2:30 P.M. on Aug. 10, 1982 under 150 foot-candle light intensity at Salinas, Calif.

CLASSIFICATION

Botanical: *Chrysanthemum morifolium,* Ramat., cv Venture.

Commercial: Spray decorative cut mum.

INFLORESCENCE

Capitulum:

*Form.*—Flat.

*Type.*—Decorative.

*Diameter across face.*—65 To 75 mm.

Corolla of ray florets:

*Color (general tonality from a distance of three meters).*—Deep yellow.

*Color (abaxial).*—9A.

*Color (adaxial).*—8B.

*Shape.*—Narrow. Oblong with rounded tip.

Corolla of disc florets:

*Color (mature).*—7A.

*Color (immature).*—154B.

Reproductive organ:

*Androecium.*—Present disc florets only; scant pollen.

*Gynoecium.*—Present both ray and disc florets.

PLANT

General appearance:

*Height.*—Tall, 80 to 90 cm., as a flowering plant from a rooted cutting, with 7 to 14 long days for May through October flowerings and maintaining a minimum nightly 13 to 14 hour continuous dark period.

Foliage:

*Color (abaxial).*—147A.

*Color (adaxial).*—147B.

*Shape.*—Deeply lobed and coarsely serrated.

CHART A

COMPARISON OF VENTURE AND GOLDEN POLARIS

| CULTIVAR | RAY FLORET COLOR | CAPITULUM FORM AND TYPE | SPRAY FORMATION |
|---|---|---|---|
| VENTURE | DEEP YELLOW | FLAT DECORATIVE | TERMINAL 12 to 15 cm. PEDUNCLES |
| GOLDEN POLARIS | MEDIUM YELLOW | FLAT DECORATIVE | TERMINAL 15 to 20 cm. PEDUNCLES |

| CULTIVAR | DIAMETER ACROSS FACE OF CAPITULUM | PLANT HEIGHT | FLOWERING RESPONSE PERIOD |
|---|---|---|---|
| VENTURE | 65 to 75 mm. | 80 to 90 cm. | 9 WEEKS |
| GOLDEN POLARIS | 65 to 75 mm. | 80 to 90 cm. | 9 to 10 WEEKS |

COMPARISONS MADE OF PLANTS GROWN AS SINGLE STEM SPRAY CUT MUMS WITH 7 LONG DAYS IN SALINAS, CALIFORNIA

I claim:

1. A new and distinct plant of *Chrysanthemum morifolium,* Ramat., named Venture, as described and illustrated, and particularly characterized as to uniqueness by the combined characteristics of flat capitulum form; decorative capitulum type; deep yellow ray floret color; diameter across face of capitulum ranging from 65 to 75 mm. at maturity; uniform nine week flowering response; tall plant height when grown single stem; 12 to 15 cm. peduncles on open, normally terminal sprays, and 13° C. minimum temperature tolerance for initiation and development of flowering buds.

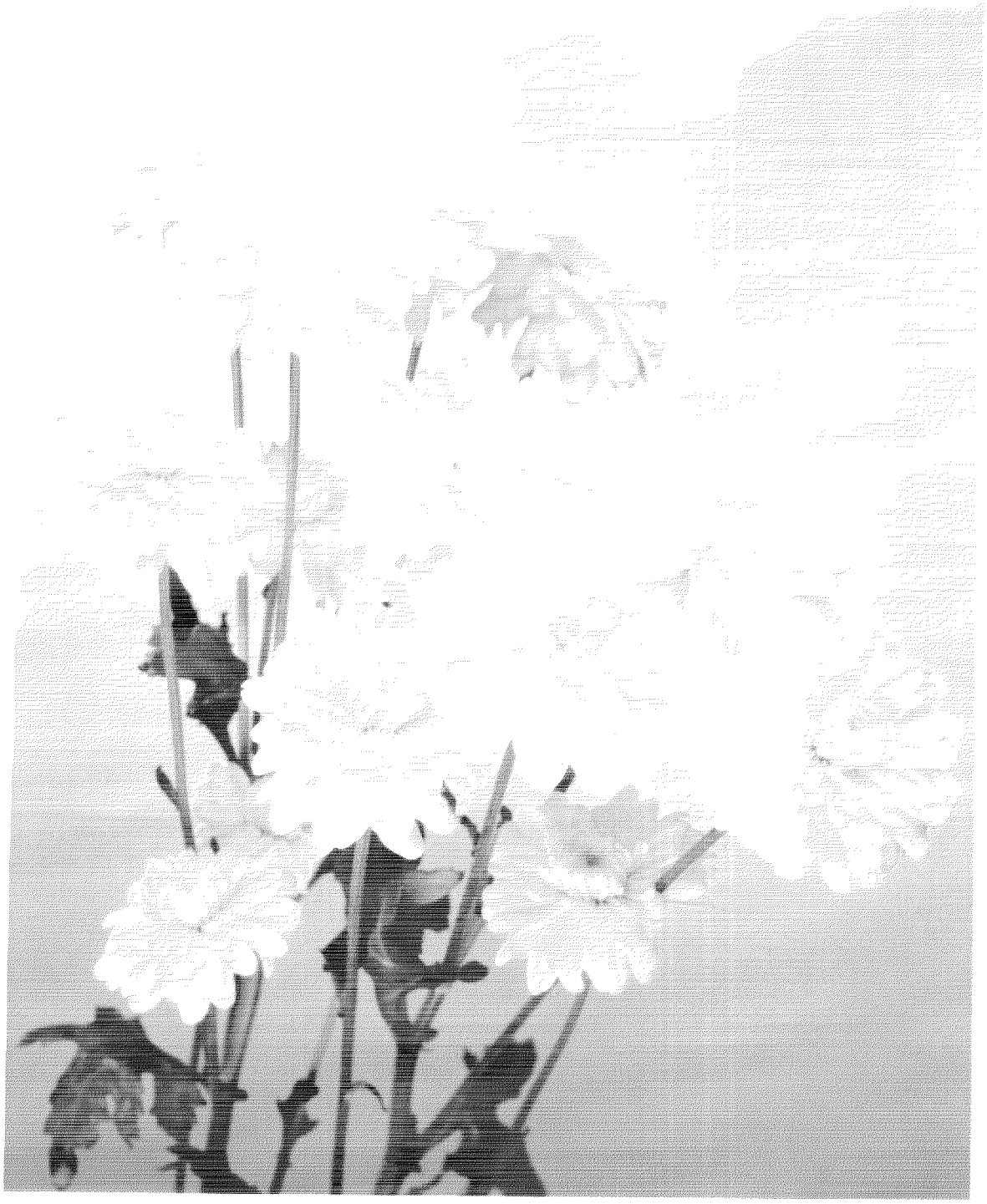

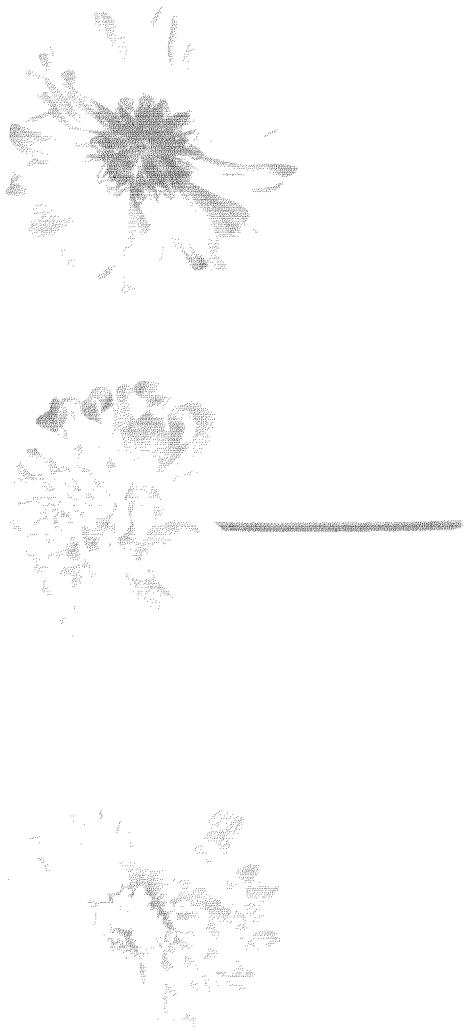

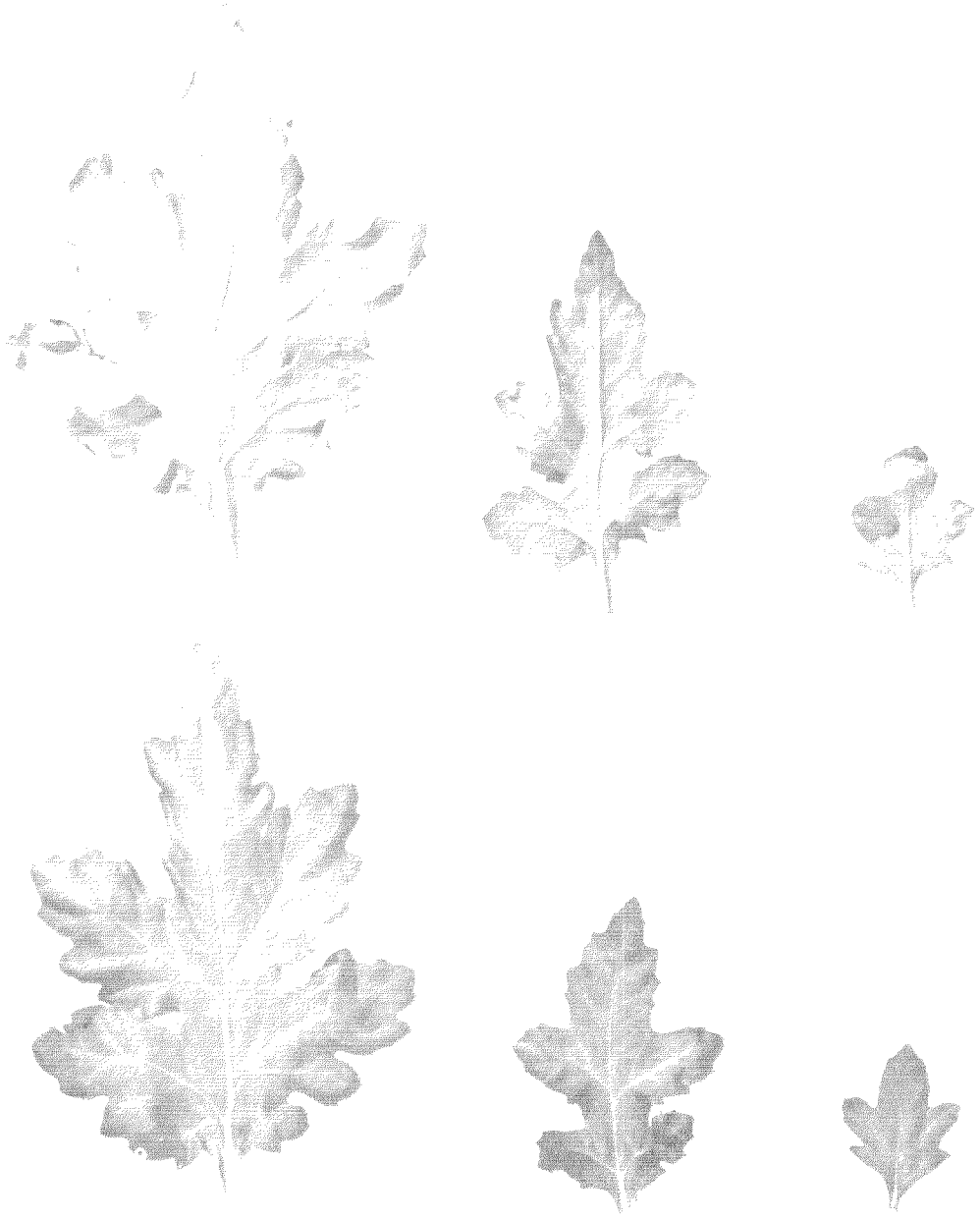

* * * * *